United States Patent
Hansen

(10) Patent No.: US 7,309,463 B2
(45) Date of Patent: *Dec. 18, 2007

(54) MOULDING METHOD, IN PARTICULAR A BLOWING AND/OR VACUUM MOULDING METHOD FOR PRODUCTION OF A DISPENSING CONTAINER FILLED WITH A MEDIUM FOR DISPENSING

(76) Inventor: Bernd Hansen, Talstr. 22-30, 74429 Sulzbach-Laufen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/723,276

(22) Filed: Mar. 19, 2007

(65) Prior Publication Data

US 2007/0187877 A1    Aug. 16, 2007

Related U.S. Application Data

(63) Continuation of application No. 10/502,748, filed on Jul. 28, 2004, now Pat. No. 7,192,549.

(51) Int. Cl.
*B29C 49/04* (2006.01)
(52) U.S. Cl. .................. 264/515; 264/524; 264/525
(58) Field of Classification Search .............. 264/515, 264/524, 525
See application file for complete search history.

(56) References Cited

U.S. PATENT DOCUMENTS 2,667,165 A    1/1954    Smith
2,667,872 A    2/1954    Smith
5,538,506 A    7/1996    Farris et al.
5,687,550 A    11/1997   Hansen et al.
6,105,342 A *  8/2000    Hansen et al. ................ 53/452

FOREIGN PATENT DOCUMENTS

DE    44 39 231 C 1    4/1996
DE    197 07 292 A 1   8/1998

* cited by examiner

Primary Examiner—Suzanne E. McDowell
(74) Attorney, Agent, or Firm—Roylance, Abrams, Berdo & Goodman, L.L.P.

(57) ABSTRACT

A moulding method, in particular a blowing or vacuum moulding method produces a dispensing container filled with a medium for dispensing. A moulding method for production of a dispensing container (1), filled with a medium for dispensing, involves introduction of an extruded plastic tube (6) into an open mould with moving main mould sections (8) and mould sections (10), cutting the plastic tube (6), spreading the plastic tube (6) into contact with the mould walls of the main mould sections (8), filling the container (1) in the mould with the medium for dispensing, introduction of a sealing unit (3), closure of the secondary mould sections (10) and subsequent moulding of the section of plastic tube (6) running through the secondary mould sections (10) to form a protective sleeve (5) which encloses a cannula (11) in the sealing unit (3) as second component of the securing device (5, 17).

7 Claims, 8 Drawing Sheets

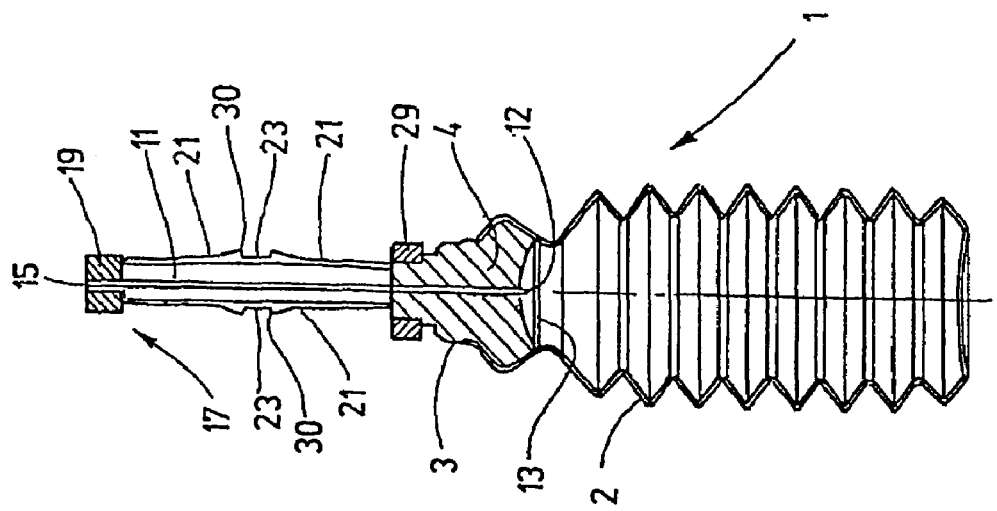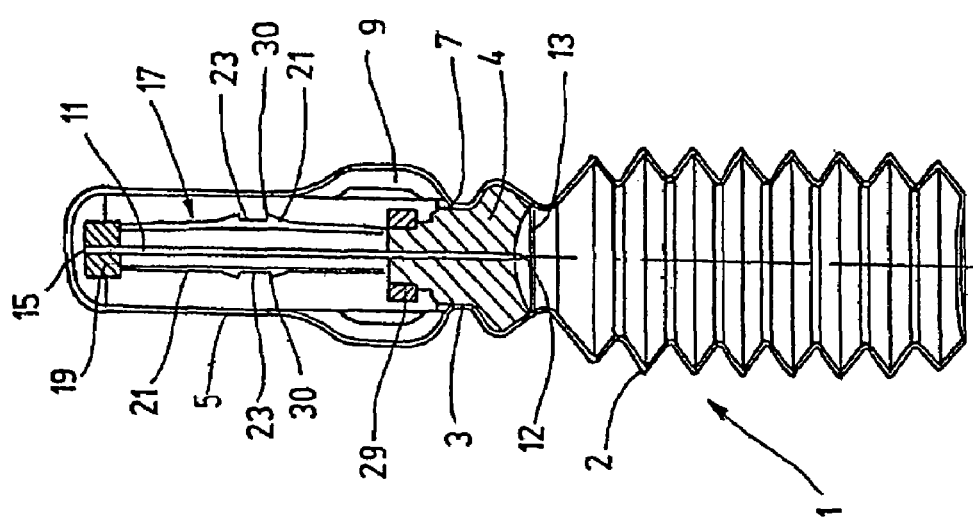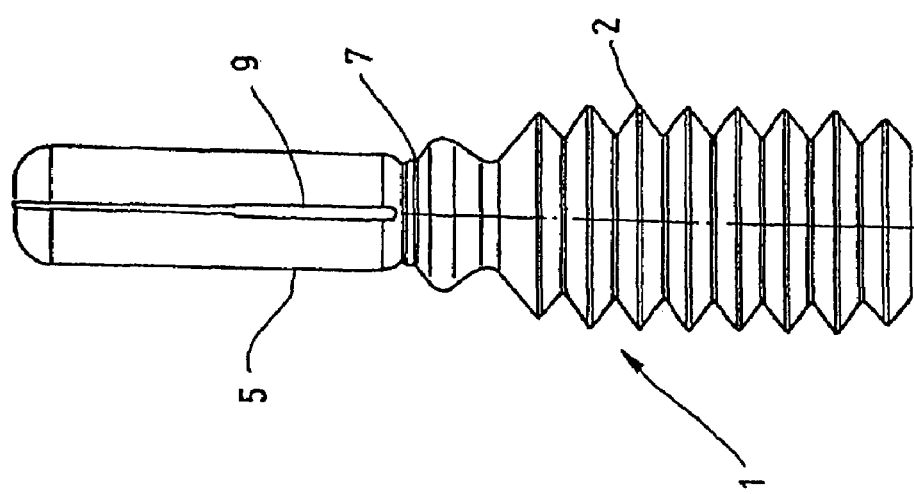

MOULDING METHOD, IN PARTICULAR A BLOWING AND/OR VACUUM MOULDING METHOD FOR PRODUCTION OF A DISPENSING CONTAINER FILLED WITH A MEDIUM FOR DISPENSING

REFERENCE TO RELATED APPLICATION

This application is a continuation of and claims the priority of U.S. patent application Ser. No. 10/502,748 filed Jul. 28, 2004 of Bernd Hansen, entitled Moulding Method, in Particular a Blowing and/or Vacuum Moulding Method for Production of a Dispensing Container Filled with a Medium for Dispensing, now U.S. Pat. No. 7,192,549, the subject matter of which is hereby incorporated by reference.

FIELD OF THE PRESENT INVENTION

The present invention relates to a moulding method, in particular a blowing and/or vacuum moulding method for production of a dispensing container filled with a medium for dispensing. The present invention relates in particular to production of a dispensing container with the primary, but not exclusive, purpose of introducing a desired volume of a medium, especially a liquid medium, into a receptacle. The medium to be introduced preferably is an additive, which, for example, is introduced as an additive admixture into a fluid present in the receptacle. The receptacle may be an infusion container with contents to be mixed with the medium as an additive.

BACKGROUND OF THE INVENTION

To mix in the medium, a syringe cannula (hollow needle) has been used to pass through a perforable seal or plug of the receptacle, such as an infusion container. Then, the medium is injected into the receptacle by expression of the syringe. This procedure requires the preliminary operational step of filling the syringe, the syringe being filled with the desired amount of the medium from a reservoir or the syringe being filled from a conventional vial holding the measured amount of the medium in question. These decanting steps are time-consuming, in that cannula and syringe must be removed from their packaging, the cannula mounted on the syringe, the vials opened or perforated, and the plunger of the syringe retracted. Considerable risk of contamination of the medium exists when these measures are carried out.

Processes permitting simultaneous formation and charging of containers by blow moulding or vacuum moulding are already known. DE 197 07 292 A1, for example, discloses such a blow moulding process.

SUMMARY OF THE INVENTION

An object of the present invention is to provide a blow moulding process or a corresponding vacuum moulding process to produce dispensing containers permitting especially simple and efficient production of such dispensing containers and producing dispensing containers permitting especially simple, rapid, and reliable dispensing of the medium from the dispensing container into a receiving container.

This object is attained by a moulding process according to the present invention where formation of the container, its charging with a particular medium, and sealing of the charged container including insertion of a sealing unit specifically designed for the dispensing process with a safety device of several components take place inside a moulding device. Consequently, at the same place of production from which only the fully finished dispensing container need be transported, the result is especially simple production in which the required sterility may be guaranteed without difficulty.

In the process of the present invention, the dispensing container containing the medium combines the integrated cannula and a protective device covering one of the projecting ends of the needle, that is, the tip of the needle, to form one integrated unit. The desired quantity of the medium involved may be made ready in the dispensing container in advance of the dispensing process. Since the tip of the needle is covered by the protective device, the container with protected cannula may be handled directly in its state of readiness for the dispensing process. Intermediate steps of decanting of medium and preparation of a syringe are not required for the dispensing process. The desired simplification, saving of time, and increased safety from contamination are thus achieved. In the case of containers produced by the process of the present invention both the risk of contamination and the risk of harm to a user, such as a nurse, are greatly reduced, since the cannula is protected by the protective device again after use.

If the outer end of the cannula is provided for perforation of a perforable seal of a receiving container to receive the medium to be dispensed, the design of the protective device of the sealing unit may be such that, after removal of the protective hood, the element protecting the cannula may be returned to its operational position by resting against the seal. When the seal is perforated by application of pressure to the protective element on the end of the cannula, the latter may be returned to its operational position and to the protective position again after withdrawal of the cannula from the seal. Handling during the dispensing process is greatly simplified as a result.

In one especially advantageous exemplary embodiment of the moulding process, the steps of expansion and charging of the container present in the mould are carried out jointly by a combined blowing-charging mandrel extending through the insertion opening. This step makes possible especially efficient production of charged containers with short cycle times.

In the course of moulding of the protective hood as an integral part of the container and as a component of the protective device, a desired point of break is moulded, preferably during closing of the mould section head jaw of the mould, in the area of transition between sealing unit and protective hood, on the wall of the latter. This point of break forms an area of separation which makes removal of the protective hood easier.

Preferably at least one projecting grip end forming a turning lever for easy manual separation of the protective hood is moulded during closing of the mould section head jaws on the protective hood.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure:

FIG. 6 is a side elevational view of an exemplary embodiment of a dispensing container produced by the moulding process of the present invention, in the operational situation preceding use, that is, with protective hood mounted;

FIG. 7 a side elevational view in section of the dispensing container of FIG. 6;

FIG. 8 a side elevational view in section of the dispensing container of FIG. 7, but with the protective hood removed;

DETAILED DESCRIPTION OF THE INVENTION

Figure 1:
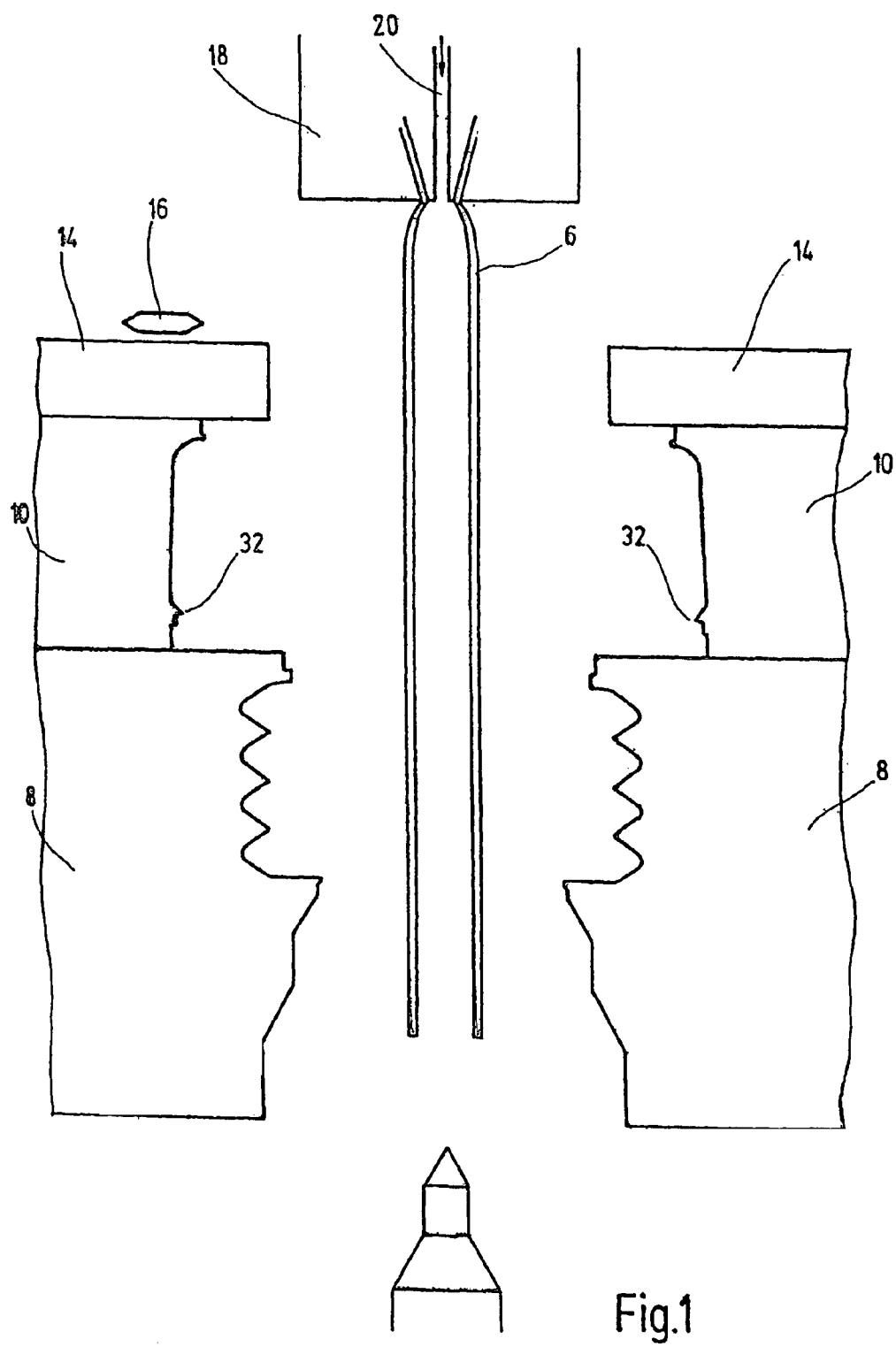
FIG. 1 is a diagrammatic side elevational view of a moulding device for a first step of practicing a process according to an embodiment of the present invention.

The figures, particularly FIGS. 6-12, illustrate an exemplary embodiment of a dispensing container 1 produced by the process of the present invention. In the exemplary embodiment shown, the dispensing container is a plastic container in the form of an ampule having a wall or body 2 provided with folds and configured as a bellows. The dispensing container 1 with that configuration may be compressed from the configuration shown in FIGS. 6 to 9 to that shown in FIGS. 10 to 12. A sealing unit 3 has been introduced into the dispensing container 1 in the neck area as an inserted component. As illustrated most clearly in FIGS. 4, 7, and 8, a cannula extends through the central area of the sealing unit 3. The inner end 12 of the cannula extends slightly inward over or beyond the body 4 of the sealing unit 3. Between the inner end 12 of the cannula 11 and the interior of the dispensing container 1, a diaphragm 13 is provided as part of the inserted portion of the sealing unit 3. In addition, a first component 17 of a cannula protective device extends along the projecting part of the cannula, and is mounted on the body 4 of the sealing unit 3. A second component of this protective device is formed by a protective hood 5, encloses the projecting part of the cannula 11 and forms an integral component of the container 1 during its production. The present invention is explained with reference to the example of a blow moulding process. Moulding of the container with protective hood 5 could also be affected by a vacuum moulding process or a combined blowing/vacuum moulding process.

Figure 2:
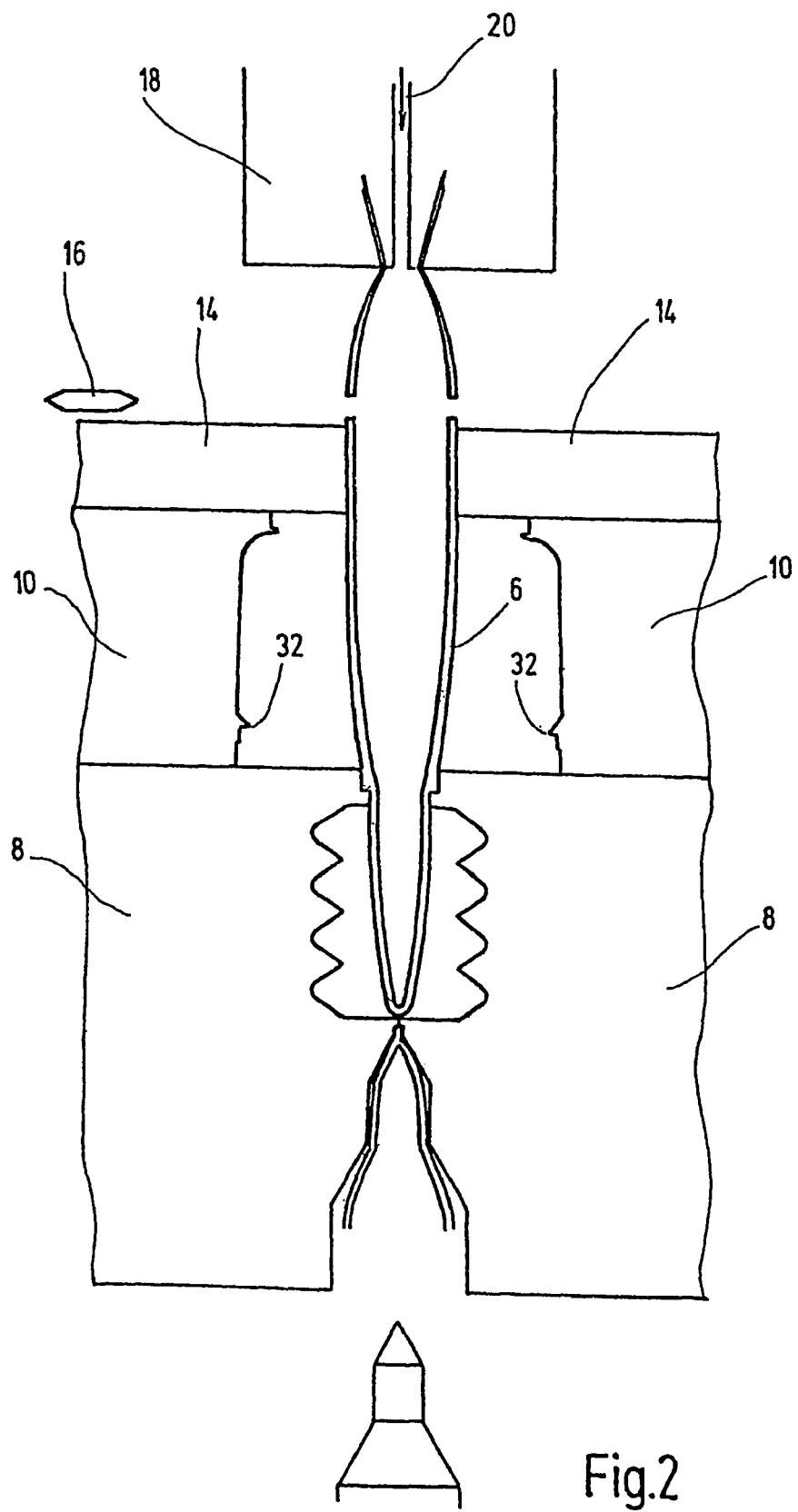
FIG. 2 is a diagrammatic side elevational view of the moulding device of FIG. 1 for practicing a second step of the process.

The operating sequence of the moulding process is illustrated in FIGS. 1 to 5. The essential parts of a moulding device are illustrated by greatly simplified diagrams. The device has three pairs of movable mould section jaws, specifically, primary or first mould section jaws 8 for moulding the primary container component receiving a medium to be dispensed, secondary or second mould section head jaws 10 for formation of the upper container component enclosing the sealing unit 3 (in the present example the protective hood 5 of the protective device), and retaining jaws 14 for stabilization of an extruded plastic tube 6. The tube is extruded inward into the fully opened mould shown in FIG. 1 from a nozzle 18 which has a conventional connection 20 for delivery of support air. After the extrusion of the tube, the primary mould section jaws 8 are closed and the retaining jaws 14 are moved onto or against the tube 6 and hold the tube 6 in a stable shape by a vacuum. The tube is separated in the section between nozzle 18 and retaining jaws 14 by the knife 16. The stage of the process thereby reached is illustrated in FIG. 2. The tube 6 is bonded by closing of the primary mould section jaws 8 on the leading end area for formation of the closed container bottom.

Figure 3:
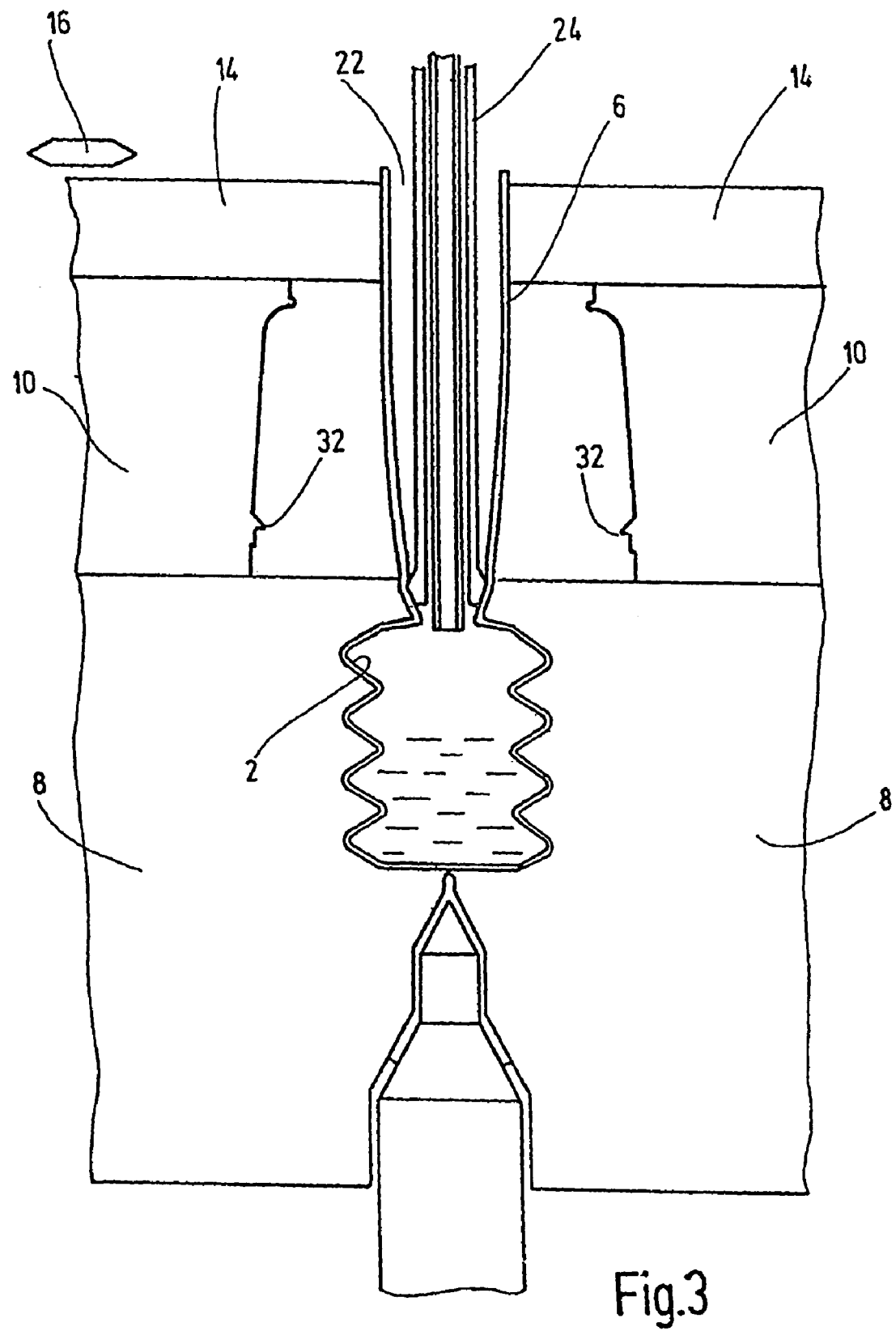
FIG. 3 is a diagrammatic side elevational view of the moulding device of FIG. 1 for practicing a third step of the process.

FIG. 3 shows that a movable combined blowing-filling mandrel 24 by which the tube 6 is expanded by blast air has been inserted through the insertion opening 22 formed by separation of the tube 6. The container wall 22 is adapted to the walls of the primary mould section jaws 8 in a bellows-like configuration. After the interior of the container has been shaped, the medium to be dispensed is introduced by the combined blowing-filling mandrel 24 (see FIG. 3).

Figure 4:
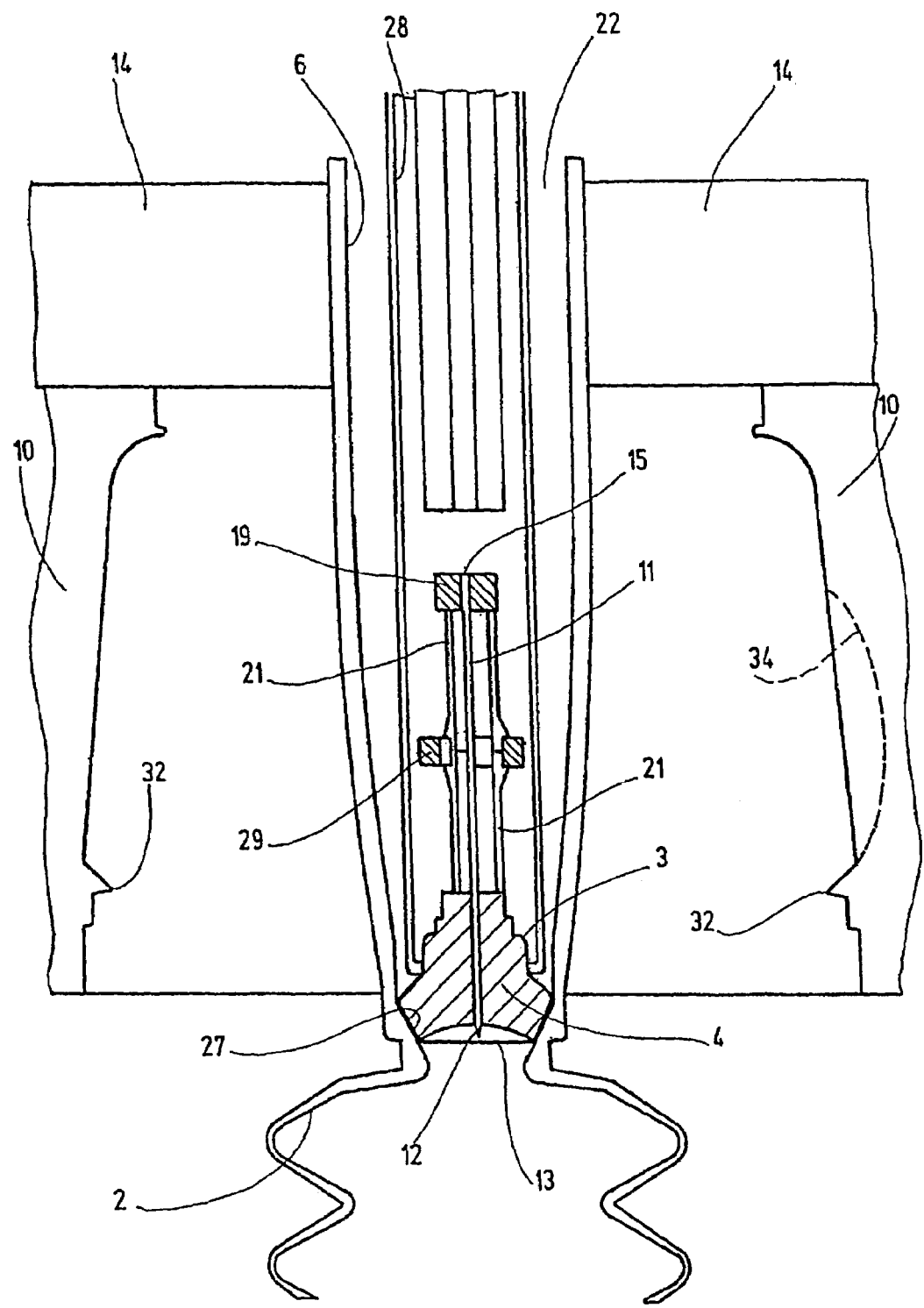
FIG. 4 is an enlarged, side elevational view in section illustrating the process step of introducing a sealing unit associated with the container.

In the immediately following process step, the sealing unit 3 is inserted by a movable vacuum gripper 28 introduced through the insertion opening 22 (see FIG. 4). As illustrated, the body 4 of the sealing unit 3 has a tapered surface which rests against a seat 27 formed by the inner wall of the tube 6 in the area in which the mould walls of the primary mould section jaws 8 adjoin the mould section head jaws 10.

Figure 5:
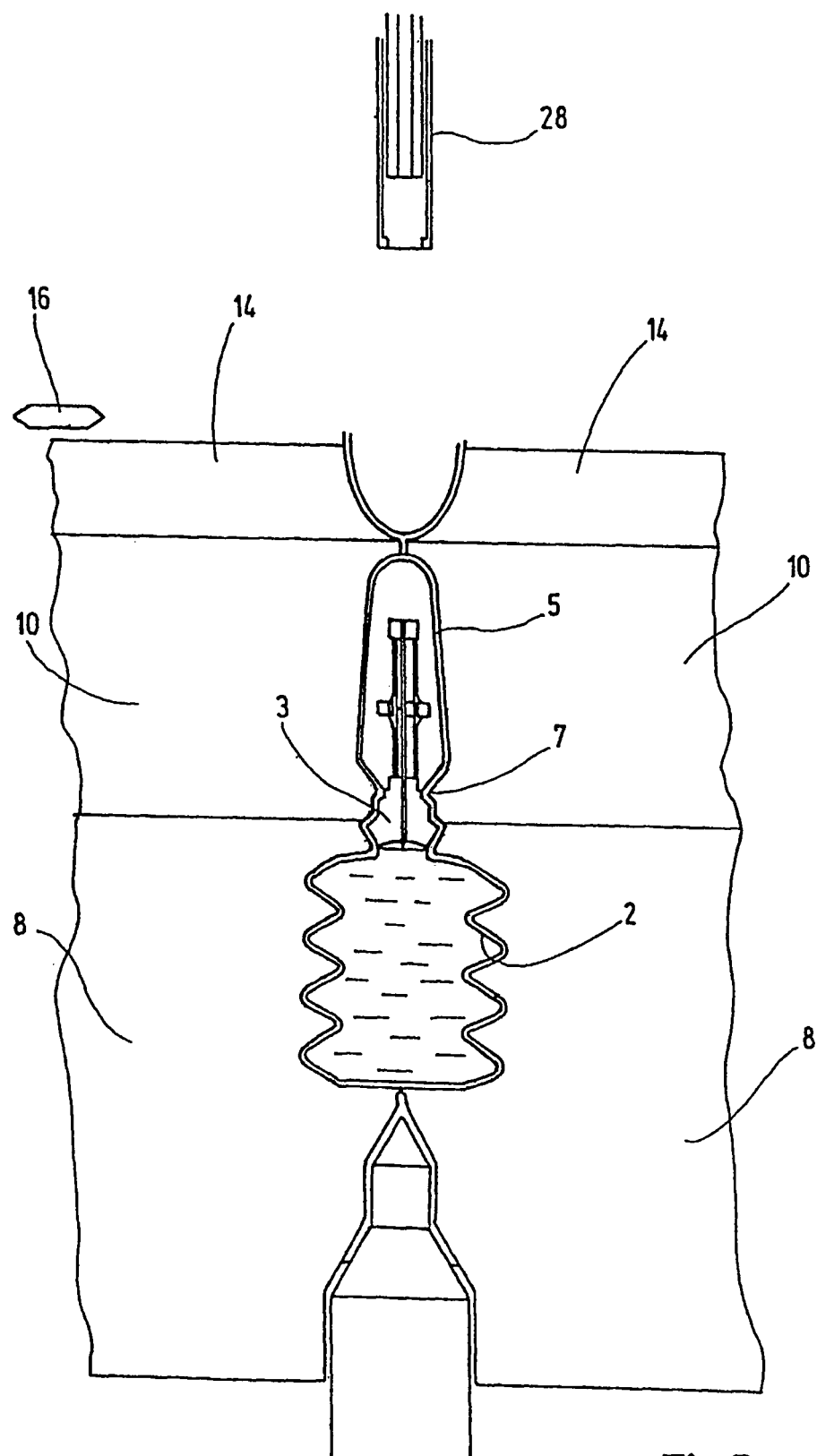
FIG. 5 is a diagrammatic side elevational view, on the scale of FIGS. 1 to 3, showing the moulding device during the step of moulding a protective hood enclosing the sealing unit.

FIG. 5 shows that subsequently in the process, the vacuum gripper 28 is moved away and upward after the insertion process has been completed. The mould is now closed as a result of establishment of contact of the mould section head jaws 10 with each other, so that the section of the tube 6 extending in the area of the mould section head jaws 10 is moulded to the protective hood 5.

As is to be seen the most clearly from the enlarged scale in FIG. 4, the mould section head jaws 10 have a mould projection 32. When the mould section head jaws 10 are closed, mould projection 32 forms an annular notch in tube 6. The notch forms a desired point of break 7 at which the protective hood 5 may be conveniently separated from the rest of the container. As seen in FIGS. 6 and 7, on the outside of the protective hood 5, a turning lever 9 is formed as a handle permitting convenient manual rotation of the protective hood 5. The mould section head jaws 10 have, in diametrically opposite positions, recesses for the purpose of forming two opposite levers 9. Only one of these recesses 34 is shown in FIG. 4, by a broken line.

Additional details of the cannula protective device 17 covered by the protective hood 5 has first and second components illustrated in FIG. 4 and FIGS. 7 to 12. They are to be described in detail with reference to FIGS. 7 to 12.

The cannula 11 extends from the outer end of the body 4 of the sealing unit 3 over a length which corresponds more or less to the length of a syringe cannula. FIGS. 6 and 7 illustrate operational situations in which the projecting outer end 15 of the cannula 11 is covered by the protective device 17 and by the protective hood 5.

Components of protective device 17 are integrally moulded on the body 4 of the sealing unit 3, and have an annular element 19 movable on the cannula 11 to a protective position (see FIGS. 7, 8, and 12) on the outer end 15 of the cannula 11 so as to cover this end of the cannula, that is, the tip of the needle. The annular element 19 is integrally connected to the body 4 of the sealing unit 3 by rod-shaped bearing elements 21. The points of connection to annular element 19 and body 4 of the sealing unit 3 are in the form of flexible joints. In addition, at approximately one-half the length of the bearing elements 21, flectors or flexible joints 23 divide the bearing elements 21. If the annular element 19 is displaced from the protective position to a service or operating position of the dispensing container along the cannula 11 (see FIGS. 10 and 11), the sections of the bearing elements 21 adjoining the flectors 23 tilt so that they are forced away from the cannula 11 and move back together as shown in FIG. 10.

Figure 9:
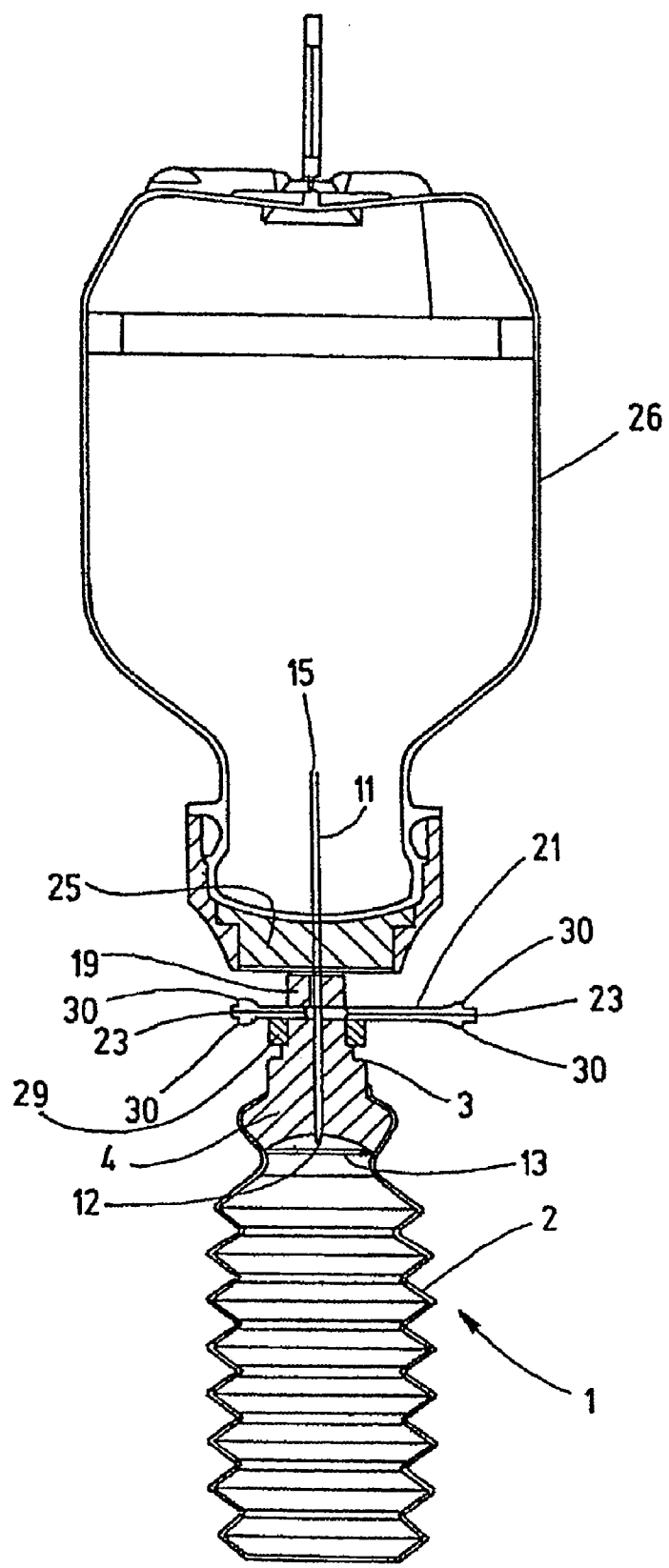
FIG. 9 a side elevational view in section of the dispensing container of FIG. 6 in an operating state in which a dispensing cannula of the dispensing container has punctured a perforable sealing plug of an infusion container.
Figures 10, 11, 12:
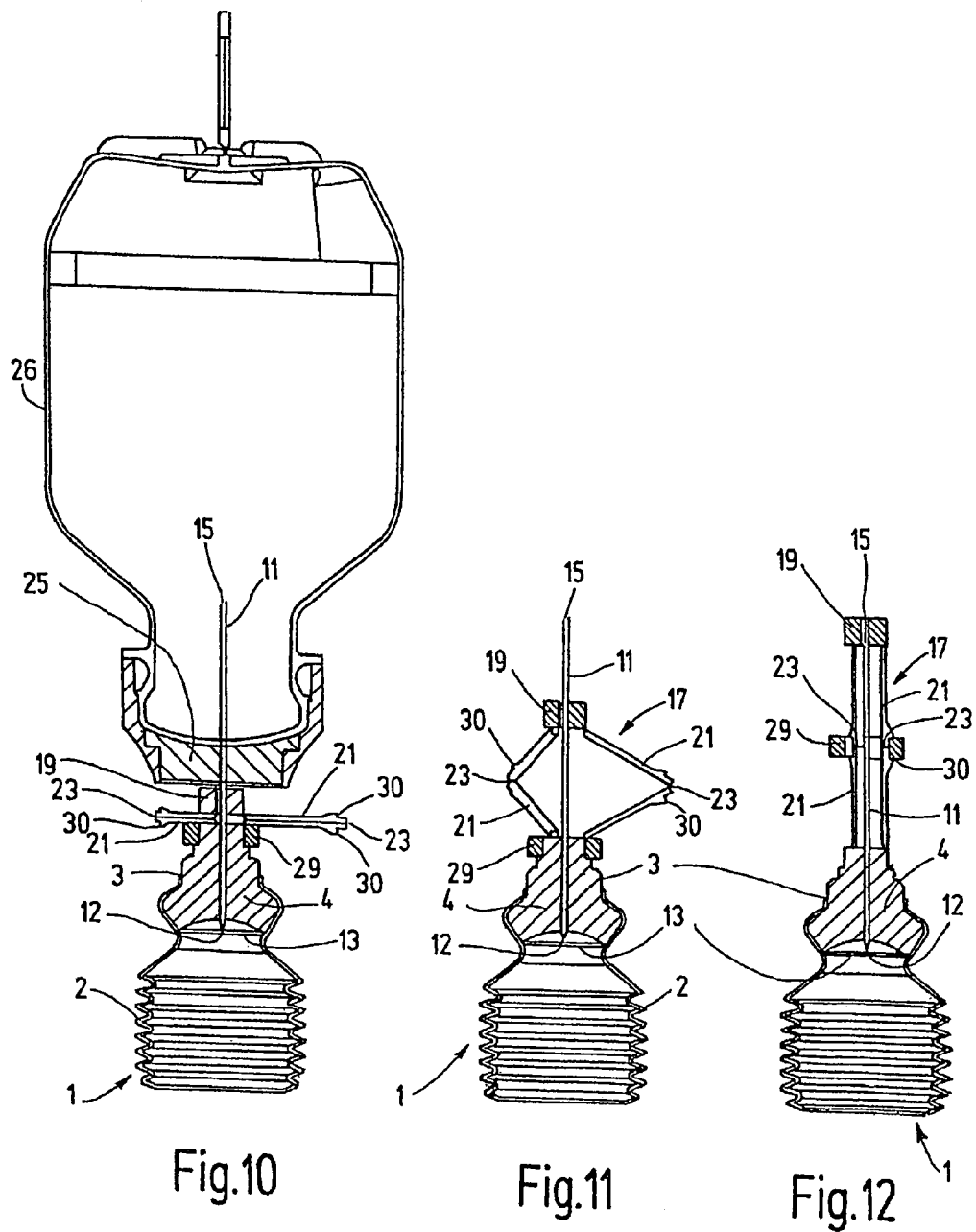
FIG. 10 is a side elevational view in section of the dispensing container and infusion container of FIG. 9, but one in which the dispensing container has been expressed for dispensing of the medium contained.
FIG. 11 is a side elevational view in section of the dispensing container of FIG. 6 in the expressed state and after removal from the sealing plug.
FIG. 12 is a side elevational view in section of the dispensing container of FIG. 11 in an operating state corresponding to the protective position of one of the components of the protective device.

FIG. 10 and FIG. 9 show the container in the situation in which front end 15 of the cannula 11 has perforated a perforable seal 25 of an infusion container 26. The annular element 19 has been forced back from the protective position oriented toward the end 15 along the cannula 11 into the operating position. The pressure of the medium present in the dispensing container 1 is increased by compression of the bellows-like wall 2 of the container (see FIG. 10), so that the diaphragm 13 is pressed against the opposite end 12 of the cannula 11 and is perforated by end 12. Compression of the dispensing container 1 results in expression of the medium present in this container into the infusion container 26, so that an amount of an additive or agent corresponding the content of the dispensing container 1 is mixed with the contents of the infusion container 26. For perforation of the diaphragm 13, the cannula 11 in the body 4 of the sealing unit 3 could also be guided for displacement limited by stops (not shown) in such a way that the cannula 11 is forced back on perforation of the seal 25 to the extent that its end 12 perforates the membrane 13.

FIG. 11 illustrates the operational situation after the expressed dispensing container 1 has been moved back and away from the seal 25 of the infusion container 26. As a result of the inherent elasticity of the bearing elements 21, the annular element 19, which previously had been forced back from the protective position during insertion of the cannula into the seal 25 is now automatically advanced or biased by the force of elasticity to some extent toward the end 15 of the cannula 11.

FIG. 12 illustrates the operational situation of the container after it has been used. The projecting outer end 15 of the cannula 11 is again secured by the protective device 17, even though the protective hood 5 is no longer in position. For this purpose, a removable protective ring 29 seated on the body 4 of the sealing unit 3 is removed from the body 4 of the sealing unit and advanced along the cannula 11. Ring 29 is slid over the bearing elements 21, approaching the cannula from the position shown in FIG. 11. The annular element 19 is advanced to the end 15 of the cannula 11. The bearing elements 21 have stop notches 30 moulded on the flectors 23. Notches 30 receive and catch the protective ring 29 (see FIG. 12).

After the protective ring 29 is caught in the stop notches 30 on the flectors 23 of the bearing elements 21, the cannula 11 is again covered by the annular element 19. Annular element 19 covers cannula end 15 despite removal of the protective hood 5, so that the container, now empty, may be safely disposed of. The dispensing container may be used to advantage, not only for admixing desired volumes of liquid media into infusion containers, but equally for dispensing liquid, semisolid, or gaseous and/or particle-charged media, to the extent that dispensing by cannulas is possible or necessary.

While one embodiment has been chosen to illustrate the invention, it will be understood by those skilled in the art that various changes and modifications can be made therein without departing from the scope of the invention as defined in the appended claims.

What is claimed is:

1. A moulding method for a blowing and/or vacuum forming of a dispensing container filled with a medium to be dispensed, the method comprising the steps of:
    extruding a plastic tube into an opened mould having movable primary mould section jaws and movable secondary mould section head jaws;
    cutting the plastic tube in an area located outside the primary and secondary mould section jaws to form an insertion end opening in the plastic tube;
    closing the primary mould section jaws (8) for formation of a mould cavity for a dispensing container body and heat sealing of the plastic tube at an end opposite the end opening for formation of a container bottom;
    expanding the plastic tube against mould walls of the primary mould section jaws by at least one of blowing of air through the insertion opening and by generating a vacuum on the mould walls to form the container body;
    charging of the container body in the mould with the medium to be dispensed;
    introducing a sealing unit through the insertion opening and into a section of the plastic tube extending through the secondary mould section jaws, the sealing unit having a dispensing cannula with a projecting outer end through which the medium is to be dispensed and a cannula protective device mounted adjacent the cannula and movable between an advanced protective position and a retracted service position; and
    closing of the secondary mould section head jaws and thereby moulding of a section of the plastic tube extending through the secondary mould section jaws to form a protective hood enclosing the cannula of the sealing unit and the protective device.

2. A moulding method according to claim 1 wherein
    the expanding and charging of the container body present in the mould are carried out jointly by a combined blowing-filling mandrel extending through the insertion opening.

3. A moulding method according to claim 1 wherein
    when the secondary mould section jaws are closed in a transitional area between the sealing unit and protective hood, a point of break is formed on a wall of the protective hood.

4. A moulding method according to claim 3 wherein
    when the secondary mould section jaws are closed on the protective hood, at least one projecting toggle is formed as a turning lever for separation of the protective hood at the point of break.

5. A moulding method according to claim 3 wherein the sealing unit with a sealing element is introduced into a seat formed by mould wall sections of the primary mould section jaws when closed adjoining the secondary mould section jaws.

6. A moulding method according to claim 5 wherein the sealing unit is introduced such that the sealing element extends through the seat formed by the primary mould section jaws and along the cannula in an area of the secondary mould section jaws.

7. A moulding method according to claim 6 wherein the point of break is formed at a distance from the seat for the sealing element and encircles the sealing element in an area into which the secondary mould section jaws extend.

* * * * *